United States Patent [19]

Tóth

[11] Patent Number: 6,048,843
[45] Date of Patent: Apr. 11, 2000

[54] TOPICAL COMPOSITION CONTAINING AMINO ACID IN COMBINATION WITH EITHER INTERFERON OF THYMIDINE DERIVATIVES FOR TREATING VIRAL OR INFLAMMATION DISEASES

[76] Inventor: Sándor Tóth, Vértói u. 3., H-6724 Szeged, Hungary

[21] Appl. No.: 09/043,657

[22] PCT Filed: Jul. 3, 1997

[86] PCT No.: PCT/HU97/00035

§ 371 Date: Jun. 16, 1998

§ 102(e) Date: Jun. 16, 1998

[87] PCT Pub. No.: WO98/04280

PCT Pub. Date: Feb. 5, 1998

[30] Foreign Application Priority Data

Jul. 25, 1996 [HU] Hungary .................................. 9602024

[51] Int. Cl.⁷ ........................ A61K 31/70; A61K 31/195
[52] U.S. Cl. ........................ 514/50; 514/561; 514/562
[58] Field of Search ................................ 514/2, 561, 562, 514/50

[56] References Cited

U.S. PATENT DOCUMENTS 4,710,376  12/1987  Evans et al. .
4,880,785  11/1989  Szabolcs nee Borbas et al. .
5,236,704   8/1993  Fujioka et al. .......................... 424/85.1

FOREIGN PATENT DOCUMENTS 0326151   8/1989  European Pat. Off. .
WO9008540 8/1990  WIPO .

OTHER PUBLICATIONS

Jones et al., Lancet, vol. 2, No. 7977, p. 128 (Jul. 17, 1976).
Mancini et al., Transplantation Proceedings, vol. 21, No. 1, pt.2, p. 2429–2430 (Feb. 1989).
Toth et al., "Effect of Amino Acids on the Expression of Antiviral Activity of Different Types of Human Interferon", Acta Microbiologica Hungarica, vol. 32, No. 4, p. 363–368 (1985).
Toth et al., "Effect of Amino Acids on the Expression of Antiviral Activity of Different Types of Human Interferon", Acta Microbiologica Hungarica, vol. 32, No. 4, p. 369–372 (1985).

*Primary Examiner*—Raymond Henley, III
*Attorney, Agent, or Firm*—Birch, Stewart, Kolasch & Birch, LLP

[57] ABSTRACT

A medically beneficial preparation is provided which contains amino acids and is applicable for augmenting the anti-viral and anti-inflammatory effects of interferon and thimidine-analogous antiherpetic drugs, for amelioration of psoriatic symptoms, and for treating Herpes virus infections.

14 Claims, 5 Drawing Sheets

TOPICAL COMPOSITION CONTAINING AMINO ACID IN COMBINATION WITH EITHER INTERFERON OF THYMIDINE DERIVATIVES FOR TREATING VIRAL OR INFLAMMATION DISEASES

This application is the national phase under 35 U.S.C. §371 of prior PCT International Application No. PCT/HU97/00035 which has an International filing date of Jul. 3, 1997 which designated the United States of America, the entire contents of which are hereby incorporated by reference.

Subject of the patent a medically beneficial preparation for external use containing amino acids.

The preparation according to the patent description is advantageously applicable for augmentation of the antiviral and anti-inflammatory effects of interferons and thimidine-analogous antiherpetic drugs, for amelioration of psoriatic symptoms and further, it is an effective drug against Herpes virus infections.

BACKGROUND OF THE INVENTION

Interferons are natural proteins with complex biological activity. Most important of their effects are antiviral, cell proliferation inhibitory and immune response enhancing properties.

These effects are utilised in the human therapy. Interferons have therapeutic use in tumour bearing patients.

Such applications are described in the following publications: J. biol. Regul. Homeostatic Agents, 1 pp 93–99 and 177–182, 1987; Intern. J. Cancer, 1987(Suppl.1.), pp 9–13, 1987; J. Interferon Res., Spec. Issue, 1992 April, pp 109–118.

Interferons are also effective in viral infections as it can be seen in the following publications: Lancet, i, p. 128, 1976; Transplantation Proc., 21, pp 2429–2430, 1989; Interferons in the Treatment of Chronic Virus Infections of the Liver, Pennine Press, Macclesfield, 1990.

They have also been proved beneficial in certrain inflammatory diseases: Neurology, 43, pp 655–661, 1993; J. Interferon and Cytokine Res., 15, pp 39–45, 1995.

The high doses applied for reaching a single therapeutic goal, however, may often provoke numerous unnecessary side effects due to the complex actions of these proteins (J. Rheumatol., 20, pp 83–85, 1992; J. Pediatr., 120(3), pp 429–431, 1992; Clin. Exp. Immunol., 90(3), pp 363–367, 1992).

These side effects are quite often dose-limiting factors in the therapeutic use of interferons.

Typically, interferons are applied in combination for therapeutic purposes in order to decrease the severity of side effects. Several different approximations are applicable for combination therapies such as: decrease in the necessary (loses by complementation with drugs of similar mechanism of action (J. Natl. Cancer Inst., 83 pp 1408–1410, 1991); combination with drugs of antagonistic mechanism of action in order to selectively reduce harmful side effects (J. Biol. Resp. Modifiers, 5, pp 447–480, 1986); selective augmentation of the required therapeutic effect by addition of potentiating components or by application of appropriate physical conditions, e.g. hyperthermia (Proc. Soc. Exp. Biol. Med., 169, pp 413, 1982).

It is known from the publications that effective therapeutic application of thimidine-analogous drugs (deoxyuridine derivatives substituted at the 5 position) with antiherpetic action is seriously limited by that fact that a fast viral resistance develops in response to therapeutic concentrations of these drugs. Viral strains resistant to one given drug show crossresistance to other ones with similar chemical structure. Dose reduction of these drugs—if it could be achieved—would reduce the selection pressure on the viruses, thereby reducing, the frequency of the development of resistant mutants and consequently enhancing the therapeutic value of the known antiherpetic agents.

SUMMARY OF THE INVENTION

The purpose of this invention is to enhance selectively the antiviral effects of interferons and antiherpetic thimidine-analogues in order to be able to decrease the effective therapeutic doses.

It was also intended to develop a drug combination beneficial in herpetic infections and effective in reducing or eliminating skin symptoms of psoriasis.

One aim of the inventions is to produce an ointment and liquid for external use which contains low dose (and, thus, free of side effects) antiviral drugs (interfernon, 5-ethyl-2'-deoxyuridine=EDU, 5-iodo-2'-deoxyuridine=IDU,) combined with components (amino acids) selectively potentiating the antiviral activity and the interferon-mediated inhibition of inflammation.

Our invention is based on the recognition that some amino acids are able to potentiate the antiherpetic effect of the thimidine analogue drugs by a factor of several grades ($10^2$–$10^4$ times) and likewise affect the antiviral and anti-inflammatory action of interferons without influencing other biological activities of interferons. Furthermore, the preparations are effective against Herpes viruses and alleviate or eliminate psoriatic symptoms of the skin.

Therefore, the core of the invention is a preparation for external use, containing amino acids, advantageously augmenting antiviral and anti-inflammatory drug actions and being benefical in psoriasis.

The preparation is characterised by its composition, containing one or more of the amino acids listed below -D- or L-aspartic acid (Asp), cysteine (Cys), cystine (cys), glycine (Gly), oxyproline (Opr), serine (Ser), tyrosine (Tyr)- and interferon or thimidine-analogous antiherpetic drugs—preferably uridine-derivaties—as required, furthermore, known pharmaceutical vehicles, preferably solvents, preservatives or known ointment bases.

The invention is further described by the following examples.

EXAMPLE 1

A sterile solution of native human interferon alpha (HuIFN-α)—preferably from the preparation under trade name EGIFERON—was made in water at a concentration of 50000 international units/ml (IU/ml) under aseptic conditions. The solution also contained an amino acid mixture of D-Asp and L-Ser at a concentration of 5 mg/ml for each. 20 w/v % sucrose was added as a conserving agent.

EXAMPLE 2

A sterile solution of native or recombinant human interferon gamma (HuIFN-γ) was made in water at a concentration of 2500 IU/ml and 15 mg/ml of D-Asp and L-Opr. 20 w/v % sucrose was added as a conserving agent.

EXAMPLE 3

A sterile solution of IDU was made in water at a concentration of 25 μg/ml. 25 mg/ml of D-Asp was dissolved in the above solution. 20 w/v % sucrose was added as a conserving agent.

EXAMPLE 4

A sterile solution of EDU was made in water at a concentration of 25 μg/ml. 1 mg/ml of L-Ser and 500 IU/ml of native or recombinant HuIFN-γ was added to the above solution. 20 w/v % sucrose was used as a conserving agent.

EXAMPLE 5

Doses of HuIFN-α according to example 1. (at an IU/g ratio) were mixed with types and doses of amino acids described in the example 1. into a pharmaceutical ointment base (e.g. unguentum hydrophylicum) under aseptic conditions.

EXAMPLE 6

The active ingredients described in the example 2. were mixed into a vehicle according to example 5. at a ratio shown in the exapmle 2. suitably substituting "g" for "ml".

EXAMPLE 7

Figure 1:
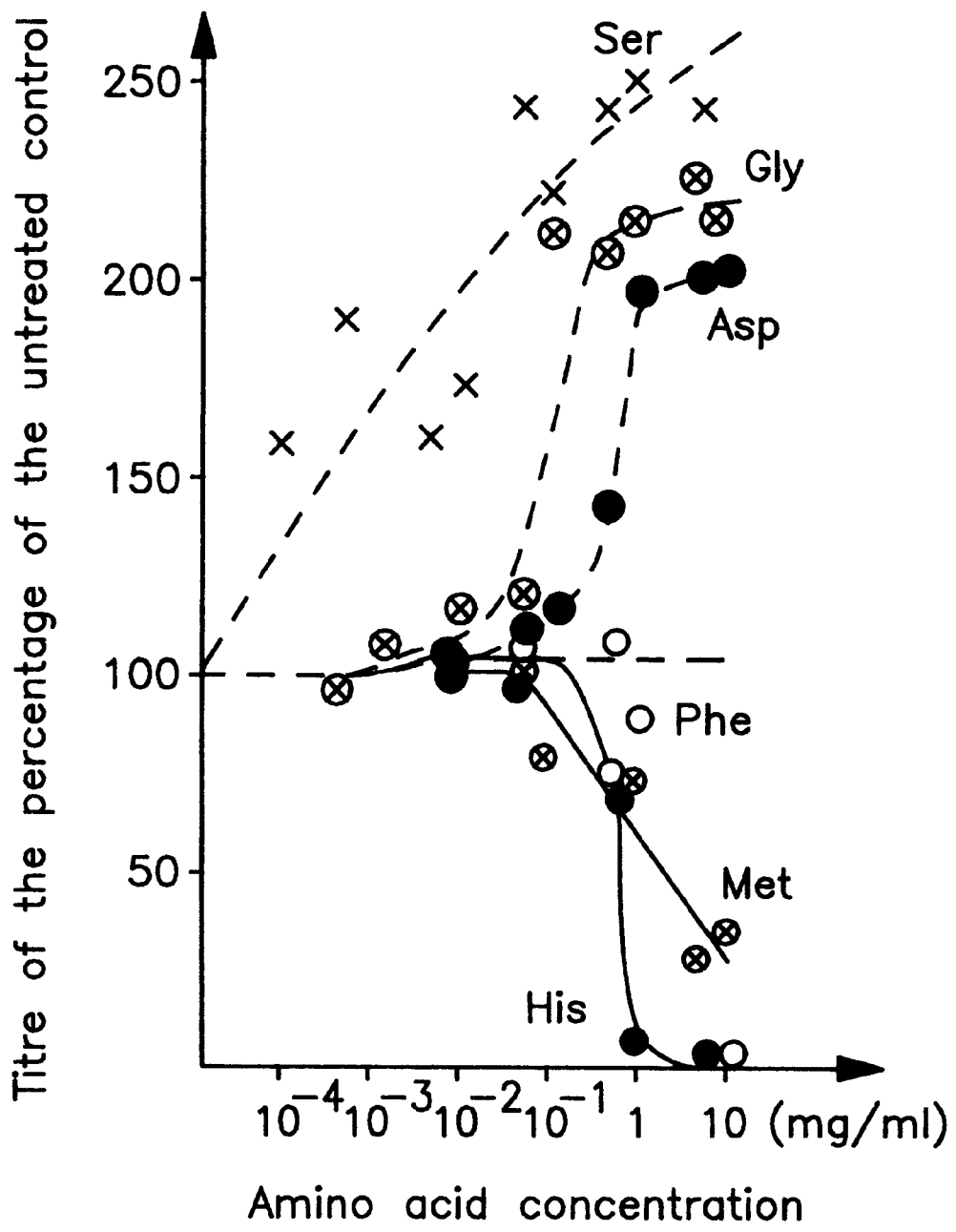
FIG. 1: The relationship between titre of the percentage of the untreated control and the amino acid concentration.
Figure 2:
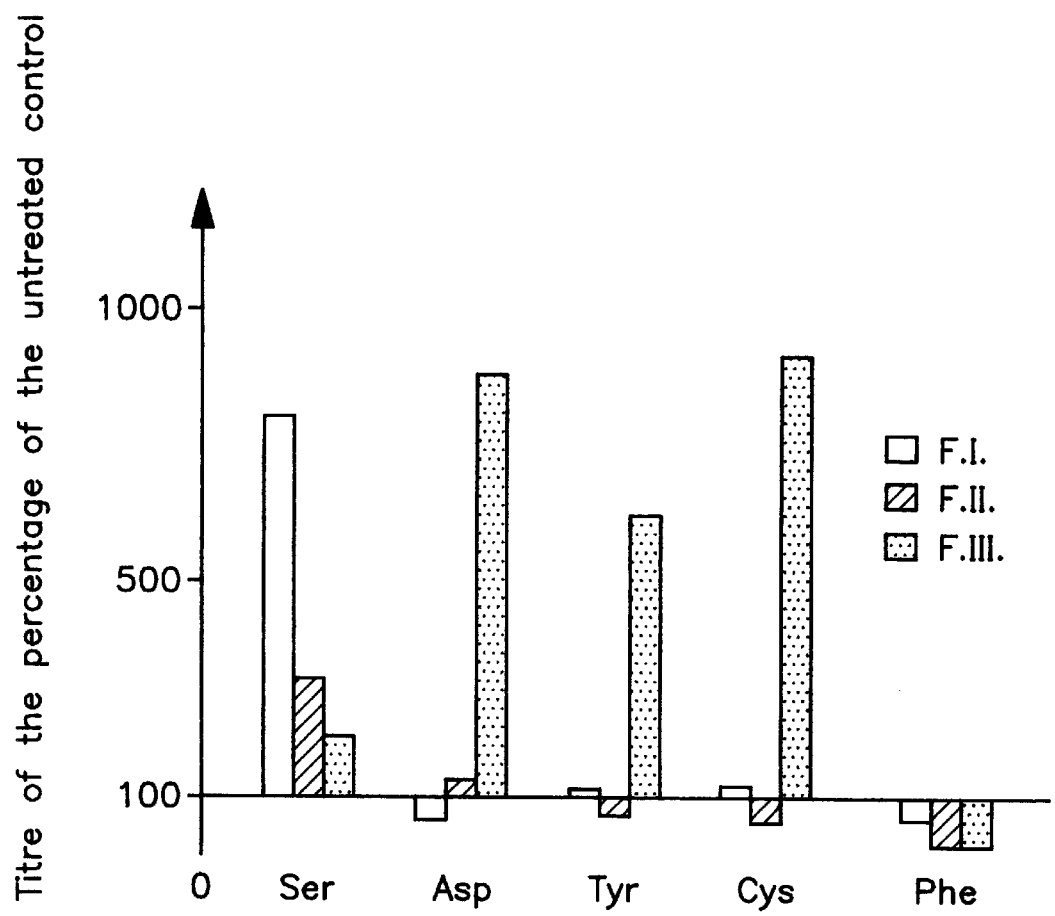
FIG. 2: The relationship between titre of the percentage of the untreated control and the amino acid concentration in phases I, II, or III.

Antiviral activity of a HuIFN-α (in a prearranged concentration of 500 IU/ml) was measured on WISH (human amnion epithelia) cells against Vesicular stomatitis virus (VSV) in the presence of different amino acids under different experimental conditions. The antiviral test consists of 3 phases. In the I. phase WISH cells are incubated in 96-well flat-bottom microplates until reaching monolayer stage. 100 μl aliquots of twofold seral dilutions of the HuIFN-α samples are then added to the test cells and are incubated for 20–24 hours at 37° C. in 5% $CO_2$ atmosphere (phase II.). Finally the IFN-treated cells are infected with a predetermined dose of VSV which can kill 100% of the unprotected WISH cells in 24 hours (phase III.). The reference point of a measurement (the titre of HuIFN-α) is that dilution of the IFN sample which provides protection for 50% of the infected cells at the end of the 24 hours infection period. The effects of different amino acids and different conditions were compared by determining the virtual titres of HuIFN-α samples having identical nominal titres. The measurements were done:

a) in the presence of different amino acids at different concentrations in phase II. (FIG. 1.)

b) in the presence of different amino acids at a concentration of 10 mg/ml in phase I., II. or III. (FIG. 2.)

c) in the presence of differenct amino acid pairs in phase II. at individual concentrations of 5—5 mg/ml (Table 1.)

TABLE 1

Antiviral titres of the IFN-α samples treated with amino acid pairs in phase II. Results are given in % of the untreated control. The synergistic co-operation of Asp-Ser and Ser-Tyr pairs should be noted.

| 1st amino acid | 2nd amino acid | | | | | |
|---|---|---|---|---|---|---|
| | None | Asp | Cys | Gly | Opr | Ser | Tyr |
| None | 100 | | | | | | |
| Asp | 152 | 171 | | | | | |
| Cys | 95 | 109 | 82 | | | | |
| Gly | 191 | 174 | 109 | 203 | | | |
| Opr | 107 | 167 | 102 | 223 | 132 | | |
| Ser | 201 | 468 | 197 | 209 | 145 | 222 | |
| Tyr | 113 | 104 | 104 | 166 | 125 | 584 | 151 | d) in the presence of different amino acid pairs in phase III. at individual concentrations of 5—5 mg/ml (Table II.)

TABLE II

Antiviral titres of the IFN-α samples treated with amino acid pairs in phase III. Results are given in % of the untreated control. Most important pairings are: Asp-Ser, Asp-Cys, and the 10 mg/ml doses of Asp, Cys, Tyr and Opr (Asp-Asp, Cys-Cys, Tyr-Tyr and Opr-Opr pairs respectively). It also should be noted that phase III. is the most similar in condition to the natural course of infections: the therapeutic drug is present simultaneously with the virus, not preceding it.

| 1st amino acid | 2nd amino acid | | | | | |
|---|---|---|---|---|---|---|
| | None | Asp | Cys | Gly | Opr | Ser | Tyr |
| None | 100 | | | | | | |
| Asp | 153 | 1722 | | | | | |
| Cys | 193 | 542 | 527 | | | | |
| Gly | 134 | 161 | 192 | 143 | | | |
| Opr | 241 | 395 | 249 | 157 | 3424 | | |
| Ser | 115 | 664 | 322 | 209 | 383 | 221 | |
| Tyr | 166 | 124 | 197 | 114 | 296 | 99 | 1568 |

EXAMPLE 8

The changes in the antiviral titres of HuIFN-γ samples upon amino acid (10 mg/ml) applications in phase II. or III. were examined in the system described in the example 7. (Table III.)

TABLE III

The effects of different amino acids applied in phase II. or III. on the antiviral titre of HuIFN-γ. High potention in phase III. by Asp, Cys and Tyr, and further, the extremely high (180-fold) augmentation by Opr can be seen.

| Amino acids | Effects in phase II. | Effects in phase III. |
|---|---|---|
| None | 100 | 100 |
| Asp | 157 | 2263 |
| Cys | 53 | 1382 |
| Gly | 99 | 184 |
| Opr | no antiviral activity | 18101 |
| Ser | 481 | 598 |
| Tyr | 101 | 1695 |

EXAMPLE 9

Figure 3:
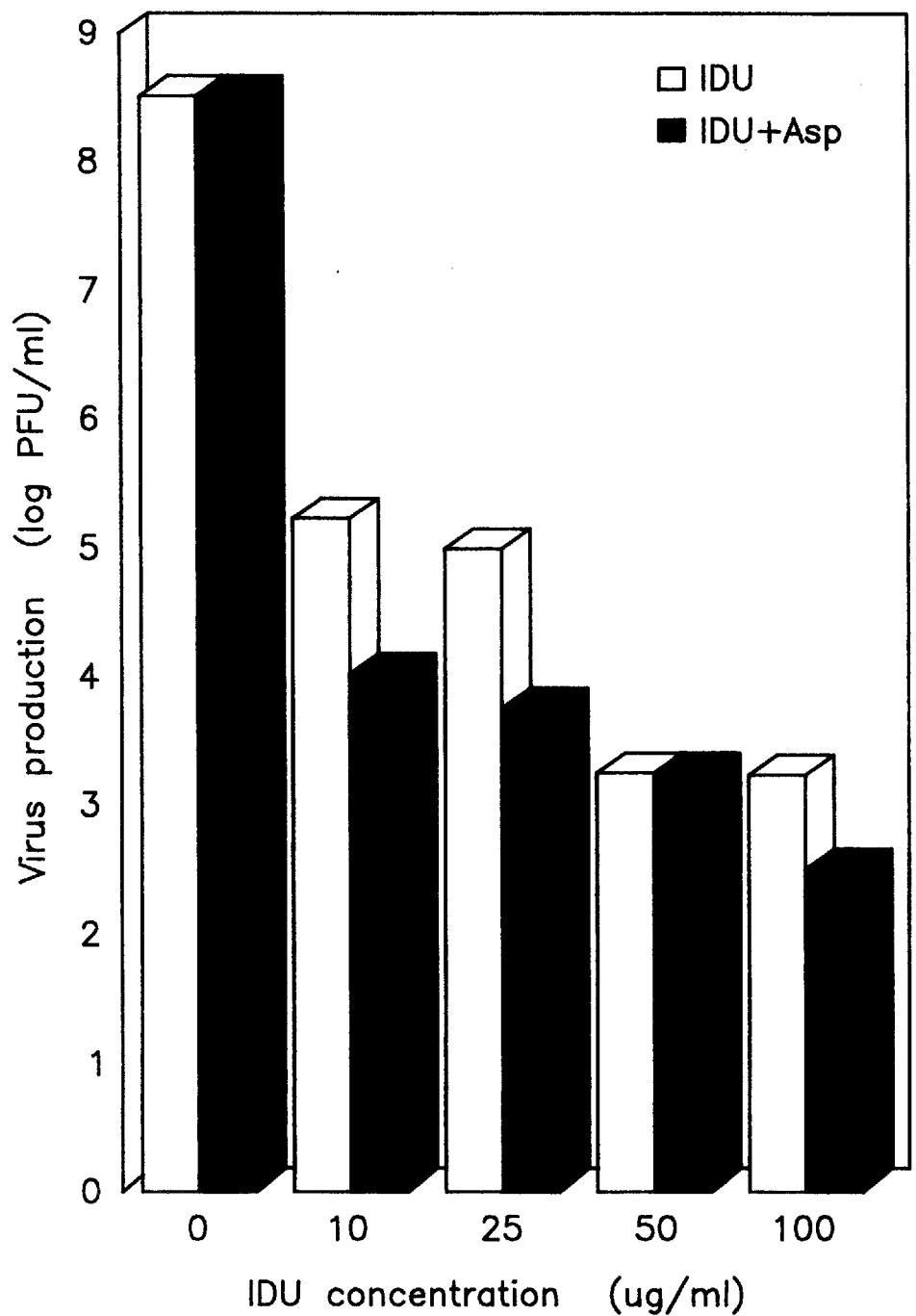
FIG. 3: The relationship between virus production and Asp in 5 mg/ml concentration.
Figure 4:
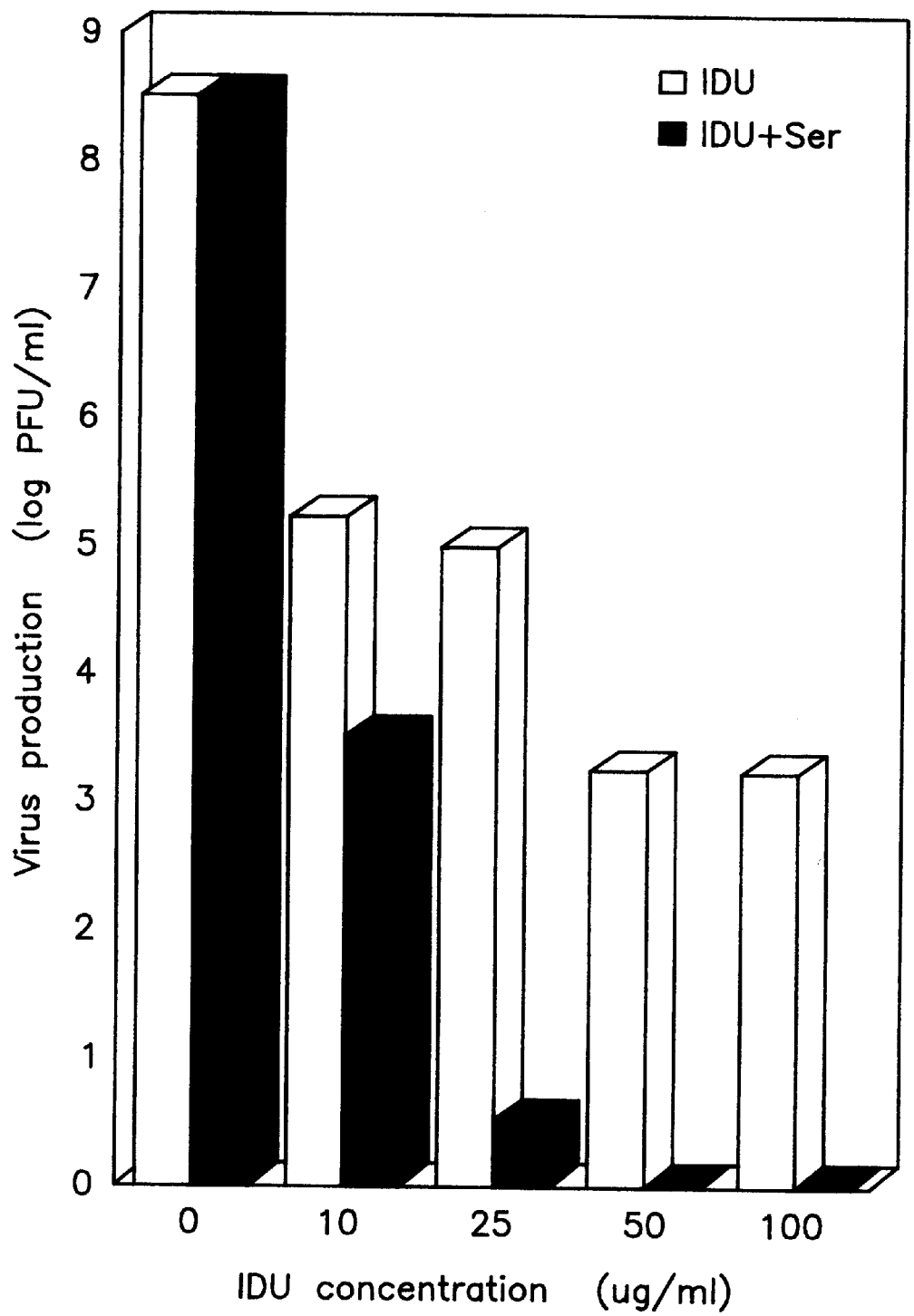
FIG. 4: The relationship between virus production and Ser in 5 mg/ml concentration.

Antiviral activities of different concentrations of IDU were measured on a permanent human tumour cell line (Hep2) against human Herpes simplex type 1. Cells were incubated in Petri dishes until monolayer stage, then were infected with a predetermined dose of the challenge virus which can kill 100% of the unprotected cells in 72 hours. The virus was allowed for 1 hour to be adsorbed on the surface of the cells. Next, a fresh nutritive medium was given to the cells containing the drug in a concentration to be tested and the experimental system was incubated for 72 hours at 37° C. in 5% $CO_2$ atmosphere. The amount of virus produced in the test system was determined as follows: infected cells were disrupted, centrifuged and the supernatants were collected. Serial 10-fold dilutions were made from the supernatants and 100 μl aliquots were measured on Hep2 monolayers in 96-well flat-bottom microplates and incubated for 72 hours, $TCID_{50}$ values (dilutions which kill 50% of the test cells at the end of the incubation period) were determined for drug treated samples as well as for untreated controls. The antiviral effects of the drugs were calculated from the differences in virus production. Changes in the antiviral activity were measured in the presence of:

a) Asp in 5 mg/ml concentration (FIG. 3.)
b) Ser in 5 mg/ml concentrtion (FIG. 4.).

EXAMPLE 10

Figure 5:
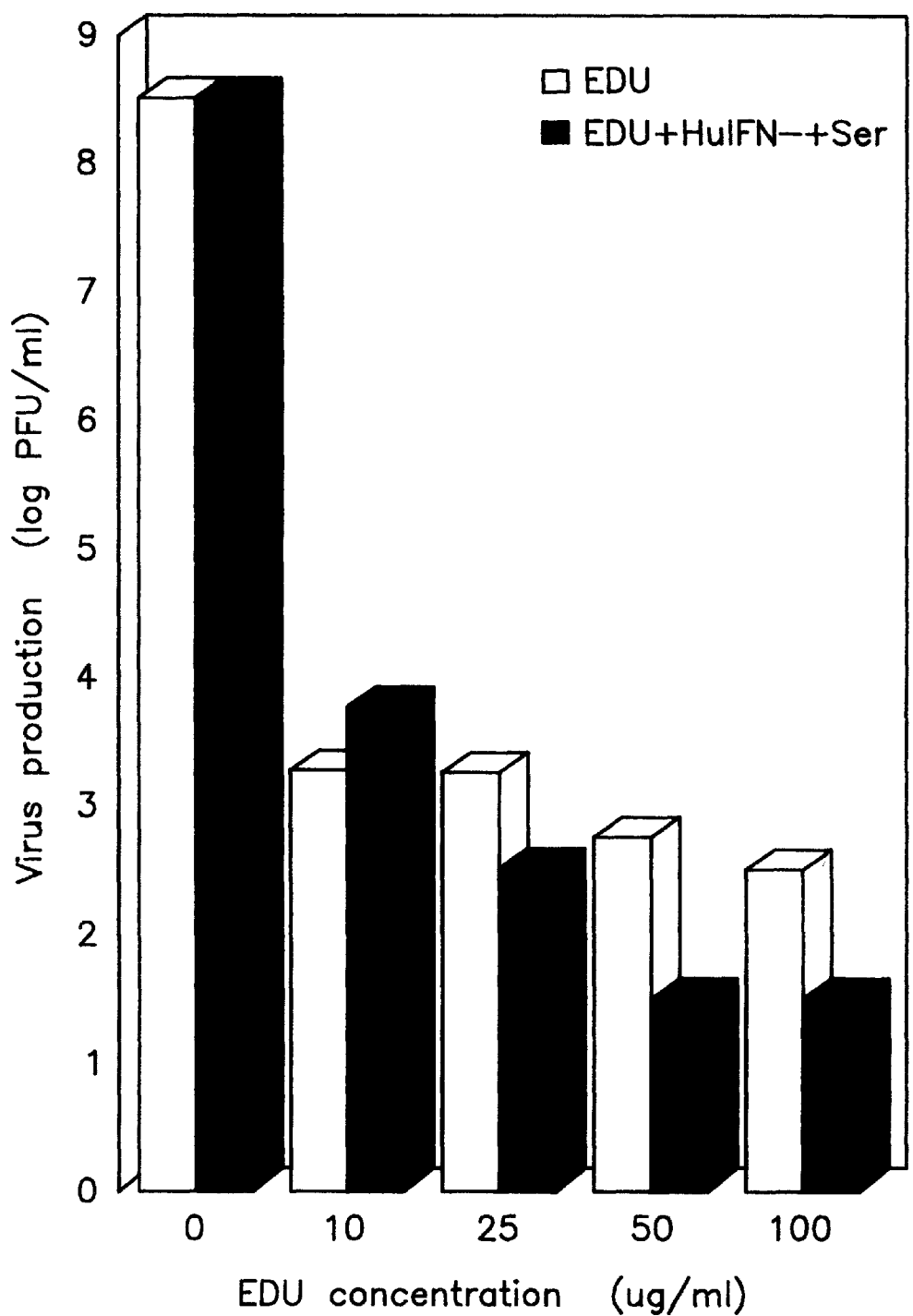
FIG. 5: The antiviral activity of different concentrations of EDU in the presence of 5 mg/ml Ser and 250 IU/ml of HuIFN-γ.

Antiviral activities of different concentrations of EDU were determined in the simultaneous presence of 5 mg/ml Ser and of 250 IU/ml HuIFN-γ (FIG. 5.) as described in the example 9.

EXAMPLE 11

Herpes virus infections (HSV 1, Herpes zoster) and inflammatory skin rushes of different aetiology were treated with an ointment described in the example 5. Patients were chosen on voluntary basis and uncontrolled treatments were carried out. The results obtained are summarised in Table IV.

TABLE IV

| Disease | Number of cases | Treatment (daily applications/ number of days) | Results | Notice |
| --- | --- | --- | --- | --- |
| labial herpes (HSV 1) | 56 cases/27 persons | 2–3/1–3 | 57/57 healings in 3 days | At 1 person vesicles extended to the neck and breast. Healing in 3 days. Ointmemt applied at the onset prevent the appearance of symptoms. |
| genital herpes (HSV 2) | 1 | 2/7 | Healing in a week | Widespread ulcerous infection on the leg. |
| zoster | 5 | 2/5 | 5/5 healings in a week | Pain quits in 24 hrs. Crusting of vesicles starts in 72 hrs. |
| postzoster neuralgia | 6 | 3/2–3 | 6/6 healings in 2–3 days | No known recurrences since 2 years. |
| decubitus | 2 | 3/2 | 2/2 healings in 2 days | Livid skin, nonulcerous state. No symptoms developed again at the treated regions during further exposition (bed-bound state). |
| acne | 17 cases/11 persons | 2–3/2–5 | 15/17 healings | Recurrence frequency decreased at treated patients. |
| exanthema migrans | 4 cases/3 persons | 3/7 | 4/4 healings in 1 week | |
| traumatic haematoma | 6 | 3/2 | 6/6 healings in 24 days | Reddening and disappearance instead of the usual coloration. |
| pruritus | 1 | 2/2 | Healing in 2 days | |
| inflammation due to irritation | 1 | 3/1 | 2/2 healings in 24 hrs. | Diaper dermatitis due to adult incontinence. |
| inflammation of surgical wounds | 1 | 3/2 | Healing in 2 days | Sterile inflammation around the sutures. |
| purulent skin inflammation | 2 | 2/1 | 2/2 healings in 1 day | Probably some anti-bacterial effects are also involved. In 1 case our treatment followed after 4 days ineffective tetracycline treatment. |
| inflammation of the outer ear cavity | 1 | 3/1 | healing in 1 day | Origin of inflammation unknown. No visible signs of infection. Treatment by earplugs. |
| "cold allergy" | 3 | 3/1 | 3/3 healings in 1 day | |
| skin rushes due to contact allergy | 4 | 2–3/3 | 4/4 healings in 3 days | Allergens were bijoux necklaces, armbands or chromium watchbands. |
| psoriasis | 7 | 2–3/2–10 | 517 healings | Not all types of disease are responsive. |

What is claimed is:

1. A medically beneficial preparation for external use comprising a thymidine-analogous antiherpetic drug; one or more amino acids selected from group consisting of D-aspartic acid, L-aspartic acid, cysteine, cystine, glycine, oxyproline, serine and tyrosine in ar amount sufficient to potentiate the antiviral activity of said thymidine-analogous antiherpetic drug; and optionally pharmaceutical additives for external use.

2. The preparation of claim 1, wherein the antiherpetic thymidine-analogous drugs are uridine derivatives.

3. The preparation according to claim 1, wherein the thymidine-analogous antiherpetic drug is 5-ethyl-2'-deoxyuridine or 5-iodo-2'-deoxyuridine.

4. A medically beneficial preparation for external use comprising a thymidine-analogous antiherpetic drug; one or more amino acids selected from group consisting of D-aspartic acid, L-aspartic acid, cysteine, cystine, glycine, oxyproline, serine and tyrosine in an amount sufficient to potentiate the antiviral activity of said thymidine-analogous antiherpetic drug; and optionally pharmaceutical additives for external use, wherein the preparation is a solution.

5. A medically beneficial preparation for external use comprising a thymidine-analogous antiherpetic drug; one or more amino acids selected from group consisting of D-aspartic acid, L-aspartic acid, cysteine, cystine, glycine, oxyproline, serine and tyrosine in an amount sufficient to potentiate the antiviral activity of said thymidine-analogous antiherpetic drug; and optionally pharmaceutical additives for external use, wherein the preparation is an ointment.

6. A medically beneficial preparation for external use comprising interferon; one or more amino acids selected from the group consisting of D-aspartic acid, L-aspartic acid, cysteine, cystine, glycine, oxyproline, serine and tyrosine in an amount sufficient to inhibit the inflammatory effects of interferon; and optionally pharmaceutical additives for external use, wherein the preparation is a solution.

7. A medically beneficial preparation for external use comprising interferon; one or more amino acids selected from the group consisting of D-aspartic acid, L-aspartic acid, cysteine, cystine, glycine, oxyproline, serine and tyrosine in an amount sufficient to inhibit the inflammatory effects of interferon; and optionally pharmaceutical additives for external use, wherein the preparation is an ointment.

8. A method of treating psoriasis, which comprises externally applying the preparation of claim 1 to a patient suffering from psoriasis.

9. A method of treating acne, which comprises externally applying an effective amount of the preparation of claim 1 to a patient suffering from acne.

10. A method of treating skin inflammation due to irritation, which comprises externally applying an effective amount of the preparation of claim 1 to a patient suffering from skin inflammation due to irritation.

11. A method of treating nonulcerous decubitus, which comprises externally applying an effective amount of the preparation of claim 1 to a patient suffering from nonulcerous decubitus.

12. A method of treating skin inflammation due to allergic conditions, which comprises externally applying an effective amount of the preparation of claim 1 to a patient suffering from skin inflammation due to allergic conditions.

13. A method of treating sterile wound inflammation, which comprises externally applying an effective amount of the preparation of claim 1 to a patient suffering from sterile wound inflammation.

14. A method of treating herpes viruses, which comprises externally applying an effective amount of the preparation of claim 1 to a patient suffering from herpes virus.

* * * * *